(12) United States Patent
Gugel et al.

(10) Patent No.: US 7,830,506 B2
(45) Date of Patent: Nov. 9, 2010

(54) METHOD FOR HIGH SPATIAL RESOLUTION EXAMINATION OF SAMPLES

(75) Inventors: Hilmar Gugel, Dossenheim (DE); Marcus Dyba, Mannheim (DE); Volker Seyfried, Nussloch (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 605 days.

(21) Appl. No.: 11/653,444

(22) Filed: Jan. 16, 2007

(65) Prior Publication Data

US 2007/0206277 A1 Sep. 6, 2007

(30) Foreign Application Priority Data

Mar. 1, 2006 (DE) .................. 10 2006 009 830

(51) Int. Cl.
*G01J 3/30* (2006.01)
(52) U.S. Cl. ...................................... 356/318
(58) Field of Classification Search .............. 356/318
See application file for complete search history.

(56) References Cited

U.S. PATENT DOCUMENTS

| | | | | |
|---|---|---|---|---|
| 4,621,911 | A * | 11/1986 | Lanni et al. ................. | 359/386 |
| 6,055,097 | A * | 4/2000 | Lanni et al. ................. | 359/386 |
| 6,255,642 | B1 * | 7/2001 | Cragg et al. ................. | 250/216 |
| 7,064,824 | B2 * | 6/2006 | Hell .......................... | 356/317 |
| 7,485,875 | B2 * | 2/2009 | Wolleschensky et al. | 250/458.1 |
| 2002/0141052 | A1 | 10/2002 | Iketaki | |
| 2002/0167724 | A1* | 11/2002 | Iketaki et al. .............. | 359/385 |
| 2006/0038993 | A1 | 2/2006 | Hell | |
| 2007/0206276 | A1* | 9/2007 | Gugel et al. ................. | 359/385 |
| 2007/0206278 | A1* | 9/2007 | Dyba et al. .................. | 359/385 |
| 2007/0268583 | A1* | 11/2007 | Dyba et al. .................. | 359/578 |

FOREIGN PATENT DOCUMENTS

| | | |
|---|---|---|
| DE | 103 25 459 | 11/2004 |
| DE | 103 25 460 | 11/2004 |
| EP | 1584918 A2 | 10/2005 |

OTHER PUBLICATIONS

Klar et al., "Breaking Abbe's diffraction resolution limit in fluorescence microscopy with stimulated emission depletion beams of various shapes", The American Physical Society, vol. 64, 066613, pp. 1-9.*
U.S. Appl. No. 11/653,446, filed Jan. 16, 2007, Dyba et al.
U.S. Appl. No. 11/623,703, filed Jan. 16, 2007, Gugel et al.
U.S. Appl. No. 11/623,690, filed Jan. 16, 2007, Dyba et al.

* cited by examiner

*Primary Examiner*—Kara E Geisel
(74) *Attorney, Agent, or Firm*—Foley & Lardner LLP

(57) ABSTRACT

A method for high spatial resolution examination of a sample, the sample to be examined including a substance that can be repeatedly converted from a first state into a second state, the first and the second states differing from one another in at least one optical property. The method includes: a) bringing the substance into the first state by means of a switching signal in a sample region to be recorded, b) inducing the second state by means of an optical signal, spatially delimited subregions being specifically excluded within the sample region to be recorded, c) reading out the remaining first states, and d) steps a) to c) are repeated, the optical signal being displaced upon each repetition in order to scan the sample, wherein the individual steps a) to d) are carried out in a sequence adapted to the respective measuring situation.

18 Claims, 1 Drawing Sheet

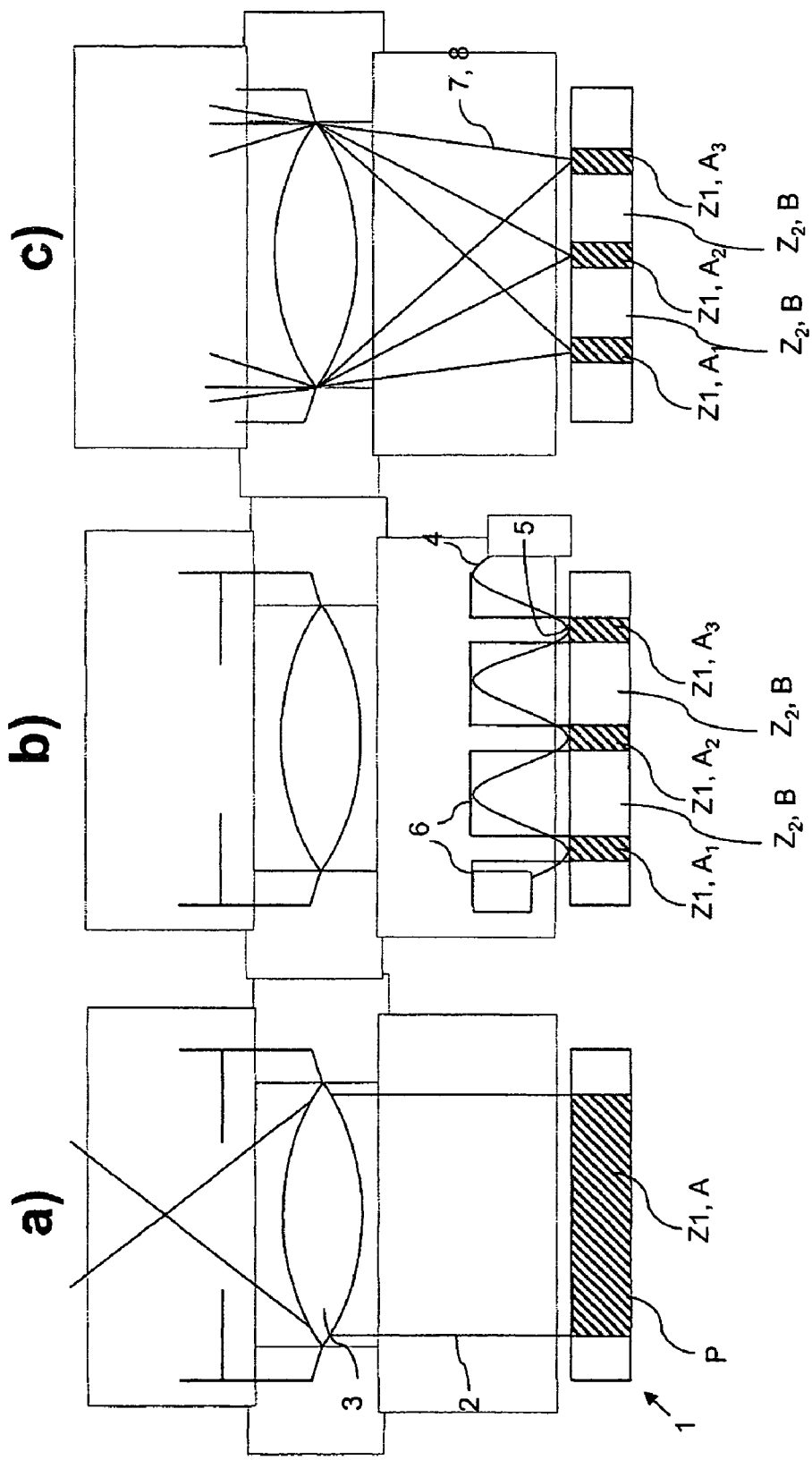

METHOD FOR HIGH SPATIAL RESOLUTION EXAMINATION OF SAMPLES

CROSS-REFERENCE TO RELATED PATENT APPLICATIONS

The right of foreign priority is claimed under 35 U.S.C. §119(a) based on Federal Republic of Germany Application No. 10 2006 009 830.7, filed Mar. 1, 2006, the entire contents of which, including the specification, drawings, claims and abstract, are incorporated herein by reference.

BACKGROUND OF THE INVENTION

The invention relates to a method for high spatial resolution examination of samples, preferably by using a laser scanning fluorescence microscope, the sample to be examined comprising a substance that can be repeatedly converted from a first state into a second state, the first and the second states differing from one another in at least one optical property, comprising the following steps:
a) the substance is brought into the first state by means of a switching signal in a sample region to be recorded,
b) the second state is induced by means of an optical signal, spatially delimited subregions being specifically excluded within the sample region to be recorded,
c) the remaining first states are read out by means of a test signal, and
d) steps a) to c) are repeated, the optical signal being displaced upon each repetition in order to scan the sample.

Methods of the type named at the beginning are known from practice. In principle, Abbe's law sets a theoretical limit to the spatial resolution of imaging optical methods owing to the diffraction limit, the diffraction limit being a function of the wavelength of the light used. However, it is possible with the aid of the methods discussed here to achieve spatial resolutions that are improved beyond the theoretical diffraction limits known from Abbe.

In the known methods, there are provided for this purpose in samples to be examined substances that can be repeatedly converted from a first state into a second state, the first and the second states differing from one another in at least one optical property. In the case of most known methods, the first state is a fluorescence-capable state (named state A below), and the second state is a nonfluorescence-capable state (named state B below). After the substance in a sample region to be recorded has been brought into the fluorescence-capable state A by means of a switching signal, state B is induced in spatially limited subregions of the sample region to be recorded by means of an optical signal, and the fluorescence of fluorescence molecules is thereby suppressed. The physical process of fluorescence suppression can be of a very different nature in this case. Thus, for example, stimulated emission from the previously excited state, or an optically induced structural change in the fluorescence molecules is known.

What is decisive is that the transition induced by an optical signal from the first into the second state in the sample volume takes place in large regions in a saturated fashion, that is to say completely, and precisely does not take place in at least one subregion of the sample volume in that the optical switching signal is specifically not irradiated there. This effect can be achieved by producing an intensity zero point of the optical signal. No transition into the second state (in general the nonfluorescing state B) takes place at the zero point and in its immediate vicinity, and so the first state (in general the fluorescing state A) is retained. Even in the close vicinity of the intensity zero points, a saturation of the transition A→B owing to the optical signal leads in the illuminated regions of the sample region to be recorded to a (virtually) complete transfer into the state B. The more strongly the process is driven into saturation, that is to say the more energy that is introduced by the optical signal into the regions around the zero point, the smaller becomes the region with fluorescence molecules in the fluorescence-capable state A, or generally in a "luminous" state. This region can be rendered arbitrarily small in principle as a function of the degree of saturation in the immediate zero point vicinity. It is therefore possible to mark regions of the state A that are arbitrarily much smaller than the smallest regions of an applied optical signal that are possible on the basis of the diffraction limit. If the region of the state A is subsequently read out, for example by irradiating a test signal, the (fluorescence-) measuring signal originates from a defined region that can be smaller than is permitted by the diffraction limit. If the sample is scanned point by point in the way described, an image is produced with a resolution that is better than is allowed by diffraction theory.

Methods of the type described here in the case of which the optical property of fluorescence capability/nonfluorescence capability is used as difference between two states are disclosed, for example, in DE 103 25 459 A1 and DE 103 25 460 A1. In these methods, fluorescence molecules are brought with the aid of an optical signal from a state A (fluorescence-capable) into a state B (nonfluorescence-capable), saturation being achieved in the transition A→B. The regions of the sample that remain in the fluorescence-capable state A result in each case from an intensity minimum, having a zero point, in the irradiated optical signal. The intensity minima are part of an interference pattern. The sample is scanned by displacing the intensity minima in the optical signal, the displacement being effected by shifting the phase of the interfering beams.

SUMMARY OF THE INVENTION

It is disadvantageous in the known methods that crosstalk, for example between the test signal and the optical signal, or between the test signal and the switching signal, can lead to a significant reduction in the resolution. Thus, crosstalk can, in particular, effect a reduction in the intensity of the fluorescence-measuring signal, or signal detection can come about that does not correspond to an actual measuring signal. Moreover, in the case of the known methods, the irradiation time for the individual signals during a cycle is limited if a spontaneous transition competes with the optical switching signal or the test signal.

The present invention is based here on an object of specifying a method of the type named at the beginning in accordance with which the negative consequences of crosstalk are as far as possible avoided with the aid of simple and cost-effective means, and a permanently high resolution is achieved.

According to the invention, the above object is achieved by means of a method having the features described herein. Consequently, the method is configured and developed in such a way that the individual steps a) to d) are carried out in a sequence adapted to the respective measuring situation.

It has firstly been recognized in the inventive approach that the occurrence of crosstalk can have an extremely disadvantageous effect on the maximum resolution that can be achieved. In a subsequent step, it was recognized that, owing to mutual influencing of the cyclically irradiated signals, crosstalk can have the consequence that the states of the substance within the sample are not set optimally in order to attain a maximum resolution. Finally, it has been recognized according to the invention that the problems described can be avoided in a simple way by carrying out the individual steps a) to d) in a sequence adapted to the respective measuring situation instead of a rigid cyclic sequence.

In a particular embodiment, it is possible, for example, to provide that a subcycle is repeatedly executed within the overall cycle, which comprises steps a) to d), the subcycle comprising only a subset of steps a) to d). Thus, for example, a subcycle comprising steps b) and c) can be repeatedly executed. This is particularly advantageous whenever the test signal leads not only to the emission of a measuring signal, but also to a changeover from second states into first states. It can then be ensured by means of a repeated execution of steps b) and c) that the sample is in the second state to an adequate extent. The sequence of steps therefore takes place as follows: a), b), c), b), c), b), c), . . . d).

In another measuring situation, a subcycle comprising steps a), b) and c) is preferably repeatedly executed. Such a repetition proves to be advantageous when the test signal leads not only to the emission of a measuring signal, but also to a changeover from first states into second states. It can then be ensured by the repeated execution of a subcycle with steps a), b), c) that the sample is adequately in the first state. The sequence of steps to be traversed is consequently as follows: a), b), c), a), b), c), a), b), c), . . . d).

In a further advantageous way, an adaptation can be performed in such a way that measuring signals that result from the reading out of first states are respectively detected only during or shortly after the emission of a test signal. It can thereby be taken into account that the switching signal and/or the optical signal can also lead to the emission of a measuring signal. However, it is not desired to detect the measuring signal that has been triggered by the switching signal and/or the optical signal, since it does not originate from the spatially narrowly delimited regions that have remained in the first state after radiation of the optical signal. Consequently, such a measuring signal does not have the desired high spatial resolution information. Detection of the named undesired measuring signals can be effectively suppressed by detecting measuring signals exclusively during/or shortly after the emission of the test signal.

Alternatively, or in addition, a detector used for detecting the measuring signals can be synchronized with the respective sequence of the steps. Likewise alternatively or in addition, a shutter can be arranged upstream of the detector, it being possible for the shutter to be synchronized with the respective sequence of the steps. In this case, the shutter can be designed as a mechanical or electronic shutter. The use of acoustooptic shutters is likewise conceivable.

The detector can be designed as a camera, in which case it can, in particular, be a CCD or an EMCCD camera. The detector can also be a photomultiplier or an APD (avalanche photodiode). The detector can likewise be designed as a detector array, in particular in the form of an APD array.

In order to attain as high a resolution as possible, it can be sensible in specific measuring situations to execute steps a), that is to say the irradiation of the switching signal, and b), that is to say the irradiation of the optical signal, in a fashion that is simultaneous or at least partially temporally overlapping. Specifically, it is important for a high resolution that irradiation of the optical signal produces within the sample regions in which the substance remains in the first state that are as small as possible. This is to happen as completely as possible, that is to say the substance is to remain as completely as possible in the first state within the regions. When the optical signal has no perfect intensity zero points, but exhibits only intensity minima that are more or less strongly expressed, the action of the optical signal also leads in the regions of the intensity minima to an—undesired—changeover of the first states into the second state. Given simultaneous action by the optical signal and the switching signal, the switching signal/optical signal ratio is large at the intensity minima in the optical signal. Consequently, these regions remain predominantly in the first state even in the case of relatively poorly formed intensity minima in the optical signal, the resolution being improved as a result.

In a preferred embodiment, the respective sequence of the steps is also synchronized with the pixel clock and/or the advancements of the imaging. In other words, both the sequence of steps in the order a), b), c), d) or a sequence in a modified order, as well as the detection of measuring signals and/or the simultaneous irradiation of the switching signal and the optical signal can be synchronized with the pixel clock and/or the advancements of the imaging. In particular, it is possible to undertake a synchronization with the advancements in the three spatial directions (x-, y-, z-image advancement). The advancements of the imaging can, for example, be implemented in this case by means of a galvanometer scanner, an acousto-optic deflector, a microelectromechanical system (MEMS) or by means of piezomechanical elements. The synchronization can preferably be implemented by means of AOTFs (Acusto-Optical-Tunable-Filter), and AOMs (Acusto-Optical-Modulator) and/or electronically and/or by means of mechanical shutters.

In a further advantageous way, a prescribable delay is set between the individual steps. This can be fixed, but freely selectable, or can be dynamically adapted to the respective measuring situation during the measuring operation. In particular, it is conceivable that the delays between individual steps be set to be of different length. A duration of different length for the individual steps themselves, that is to say the radiation periods of the respective signals, can also be different. Both the delays and the individual step periods, that is to say in concrete terms the signal irradiation times and detector readout times, can preferably be selected such that they are the same for all sample points. This is advantageous in particular with regard to a simple image evaluation, since it eliminates conversions and different weightings of individual image regions.

There are various possibilities of configuring and developing the teaching of the present invention in an advantageous way. To this end, reference is to be made to the claims arranged hereafter, and on the other hand to the subsequent explanation of a preferred exemplary embodiment of the method according to the invention for high spatial resolution examination of samples.

BRIEF DESCRIPTION OF THE DRAWINGS

Preferred refinements and developments of the teaching are also explained in general in conjunction with explanations of the preferred exemplary embodiment and with the aid of the drawing, in which the sole FIGURE shows a schematic illustration of an exemplary embodiment of a method for high spatial resolution examination of samples.

DETAILED DESCRIPTION OF THE PREFERRED EMBODIMENTS

The sole FIGURE is a schematic of steps a) to c) of a method such as is used for high spatial resolution examination of samples beyond the diffraction-limited resolving limit. In accordance with part a) of the FIGURE, the first step is to use a switching signal 2 to bring into the first state Z1 in the entire sample space P to be recorded a substance that is provided in the sample 1 and can be converted repeatedly from a first state Z1 into a second state Z2, the first and the second states Z1, Z2 differing from one another in at least one optical property. In the exemplary embodiment illustrated in concrete terms, the first state Z1 is a fluorescing state A, and the second state Z2 is a nonfluorescing state B. In the example illustrated in concrete terms, the substance provided in the sample 1 is a photochromic substance whose molecules are brought into the fluorescence-capable state A by irradiation with light of a first wavelength, the switching signal 2. This happens ideally in that the sample 1 is irradiated with the switching signal 2 (step a)) in the entire sample space P by illumination through an objective 3.

In the case of ground state depletion (GSD), the transmission into the fluorescence-capable (single) state usually takes place spontaneously. The irradiation of optical switching signals is therefore superfluous in this case, there being a need only to take account of waiting times of typically 1 to 100 µs (in part also a little longer).

In the next step—step b), illustrated in part b) of the FIGURE—light of another wavelength, the so-called optical signal 4, is applied to the sample region P to be recorded. This happens in the form of a light structure with defined intensity zero points 5. The optical signal 4 induces in a saturated fashion the transition A→B in all regions 6 illuminated with the light of the optical signal 4. In other words, it is only regions of the substance that are narrowly defined in the immediate vicinity of the intensity zero points 5 that remain in state A. The remaining regions $A_1, A_2, A_3, \ldots$ of the substance in state A can be much smaller than the dimensions of the light structure of the optical signal 4 itself, that is to say far smaller in concrete terms than diffraction-limited structures. The size of the regions $A_1, A_2, A_3, \ldots$ remaining in state A is determined entirely as a function of the quality of the intensity minima 5, and thus of the degree of saturation of the transition A→B that is achieved.

Part c) of the FIGURE is a schematic of the readout operation of state A. To this end, an optical test signal 7 is irradiated into the sample region P to be recorded in such a way that those regions prepared in step b) in accordance with part b) of the FIGURE and in which the substance has remained in state A, are recorded. Regions of the substance in state A that consequently still exist and lie outside the sample region P to be recorded may not be recorded in this case. The fluorescent light emanating from the substance in state A is detected as measuring signal 8 by a detector (not shown), a unique assignment of the detected measuring signals 8 to the individual regions $A_1, A_2, A_3, \ldots$ being undertaken.

The steps a) to c) illustrated in the FIGURE are repeated, the optical signal 4 being displaced upon each repetition in order to scan the sample 1 (step d)). According to the invention, the individual steps a) to d) are not traversed in a permanently prescribed sequence in a rigid cycle, but are, however, carried out in a sequence adapted to the respective measuring situation.

In order to avoid repetitions, reference may be made to the general part of the description and to the attached patent claims with regard to further advantageous refinements of the method according to the invention.

Finally, it may be pointed out expressly that the above-described exemplary embodiment serves merely for discussing the teaching claimed, but does not restrict the latter to the exemplary embodiment.

The invention claimed is:

1. A method for high spatial resolution examination of a sample, the sample to be examined comprising a substance that can be repeatedly converted from a first state into a second state, the first and the second states differing from one another in at least one optical property, comprising the following steps:
   a) bringing the substance into the first state by a switching signal in a sample region to be recorded,
   b) inducing the second state by an optical signal, wherein spatially delimited subregions of remaining first states are specifically excluded within the sample region to be recorded,
   c) reading out the remaining first states, and
   d) steps a) to c) are repeated, the optical signal being displaced upon each repetition in order to scan the sample,
   wherein the individual steps a) to d) are carried out in a sequence adapted to a respective measuring situation, wherein a subcycle comprising a subset of steps a) to d) is repeatedly executed within the overall cycle comprising steps a) to d).

2. The method as claimed in claim 1, wherein the repeatedly executed subcycle comprises a subset consisting of steps b) and c).

3. The method as claimed in claim 1, wherein the repeatedly executed subcycle comprises a subset consisting of steps a), b) and c).

4. The method as claimed in claim 1, wherein the reading out the remaining first states is performed by a test signal, which is different from the switching signal and the optical signal, irradiated into the sample region.

5. The method as claimed in claim 1, wherein a detector for detecting measuring signals resulting from the reading out of the first states is synchronized with the respective sequence of the steps.

6. The method as claimed in claim 1, wherein a shutter arranged upstream of a detector for detecting measuring signals resulting from the reading out of the first states is synchronized with the respective sequence of the steps.

7. The method as claimed in claim 5, wherein a CCD or EMCCD camera is used as the detector.

8. The method as claimed in claim 5, wherein a photomultiplier or an avalanche photodiode (APD) is used as the detector.

9. The method as claimed in claim 5, wherein a detector array is used as the detector.

10. The method as claimed in claim 1,
    wherein steps a) and b) are executed in a fashion that is simultaneous or at least partially temporally overlapping.

11. The method as claimed in claim 1, wherein the imaging is advanced by galvanometer scanners, acoustooptic deflectors, MEMS or piezomechanical elements.

12. The method as claimed in claim 11, wherein the respective sequence of the steps is synchronized with a pixel clock and/or the advancements of the imaging.

13. The method as claimed in claim 12, wherein the synchronization is implemented by AOTFs and/or AOMs and/or electronically and/or by means of mechanical shutters.

14. The method as claimed in claim 1, wherein a prescribable delay is set between the individual steps.

15. The method as claimed in claim 14, wherein the delays between the individual steps, and/or the duration of the individual steps are themselves set to be of different length.

16. The method as claimed in claim 1, wherein the examination is performed using a laser scanning fluorescence microscope.

17. The method as claimed in claim 4, wherein measuring signals resulting from the reading out of the first states are respectively detected only during and/or shortly after emission of the test signal.

18. The method as claimed in claim 9, wherein the detector array comprises an APD array.

* * * * *